United States Patent [19]
Milberger et al.

[11] 4,350,639
[45] Sep. 21, 1982

[54] PREPARATION OF MALEIC ANHYDRIDE

[75] Inventors: Ernest C. Milberger, Solon; Noel J. Bremer, Stow; Dennis E. Dria, Cleveland, all of Ohio

[73] Assignee: The Standard Oil Company, Cleveland, Ohio

[21] Appl. No.: 258,712

[22] Filed: Apr. 29, 1981

Related U.S. Application Data

[62] Division of Ser. No. 146,971, May 5, 1980, Pat. No. 4,333,853.

[51] Int. Cl.$^3$ ............................................. C07D 307/60
[52] U.S. Cl. ..................................................... 549/259
[58] Field of Search .................... 260/346.75; 252/435, 252/437

[56] References Cited
U.S. PATENT DOCUMENTS

| | | | |
|---|---|---|---|
| 3,985,775 | 10/1976 | Harrison | 260/346.75 |
| 4,016,105 | 4/1977 | Kerr | 252/435 |
| 4,043,943 | 8/1977 | Schneider | 252/435 |
| 4,132,670 | 1/1979 | Katsumoto et al. | 252/437 |
| 4,149,992 | 4/1979 | Mount et al. | 252/435 |

Primary Examiner—Henry R. Jiles
Assistant Examiner—Bernard Dentz
Attorney, Agent, or Firm—Joseph G. Curatolo; Herbert D. Knudsen; Larry W. Evans

[57] ABSTRACT

The present invention provides improved oxidation catalysts containing mixed oxides of vanadium and phosphorus and the method for the preparation thereof, which catalysts are particularly effective in the oxidation of n-butane, n-butenes, 1,3-butadiene or a mixture thereof with molecular oxygen or an oxygen-containing gas in the vapor phase to produce excellent yields of maleic anhydride with very good selectivity. At least one vanadium compound, a substantial portion of which is in the pentavalent state, and at least one phosphorus-containing compound is added to an organic liquid medium capable of reducing at least a portion of the vanadium to a +4 valence state, to form a reaction mixture. Partial reduction of the vanadium is effected in the presence of the phosphorus-containing compound and a highly ordered and uniform mixed vanadium phosphorus oxide-containing catalyst precursor is formed.

16 Claims, 16 Drawing Figures

($V_2O_5$)  FIG. 1

10 MICRONS 0.5 MICRONS ($V_2O_5$)  FIG. 2

(PRIOR ART) FIG. 3

5 MICRONS 0.5 MICRONS

0.5 MICRONS (PRIOR ART)    FIG. 7

5 MICRONS (PRIOR ART)    FIG. 8

5 MICRONS

FIG. 9

5 MICRONS

FIG. 10

2 MICRONS

FIG. 11

2 MICRONS

FIG. 12

0.5 MICRONS

FIG.13

0.5 MICRONS

PREPARATION OF MALEIC ANHYDRIDE

This is a division of application Ser. No. 146,971 filed May 5, 1980 now U.S. Pat. No. 4,333,853.

BACKGROUND OF THE INVENTION

This invention relates to a method for preparing catalysts useful in the production of dicarboxylic acid anhydrides by the oxidation of hydrocarbons. More particularly it is directed to the preparation of catalysts suitable for producing maleic anhydride from 4-carbon atom hydrocarbons, such as n-butane, n-butenes, 1,3 butadiene or a mixture thereof.

Catalysts containing vanadium and phosphorus oxides have been used in the oxidation of 4-carbon atom hydrocarbons, such as n-butane, n-butenes, 1,3 butadiene or mixtures thereof with molecular oxygen or oxygen-containing gas to produce maleic anhydride. Conventional methods of preparing these catalysts involve reducing a pentavalent vanadium compound, and combining the same with a phosphorus compound, and if desired, promoter element compounds under conditions which will provide or maintain vanadium in a valence state below +5 to form catalyst precursors capable of being converted to an oxide. The catalyst oxide precursor is then recovered and calcined to provide active catalytic material.

The use of gaseous HCl as a reducing agent for vanadium is disclosed in U.S. Pat. No. 4,002,650 where the vanadium and phosphorus components are reacted in an aqueous solution. The use of gaseous HCl as a reducing agent for vanadium is also described in U.S. Pat. No. 4,043,943 where the vanadium and phosphorus components are reacted in a liquid organic medium.

U.S. Pat. No. 4,016,105 describes the preparation vanadium and phosphorus oxide-containing catalysts, utilizing as reducing agents, organic acids or aldehydes, together with a co-reducing secondary alcohol. These reducing agents are added to an aqueous solution with the vanadium and phosphorus components.

Similar preparational techniques are described in European Patent Appln. No. 3,431 in which the additional step of comminuting the vanadium-phosphorus precursor to a particle size of 500 to 700 microns (0.5 to 0.7 mm) is disclosed.

The use of such reducing agents as disclosed in the art, requires special precautions in the preparation of these catalysts because of the corrosive nature of the materials utilized.

A method for preparing catalysts containing vanadium and phosphorus oxides was described in U.S. Pat. No. 4,132,670 which required the maintenance of a solid phase and dispersion of the vanadium-containing feed compound. The method includes forming a vanadium-containing compound dispersion in an organic liquid medium such as alcohols, aldehydes, ketones, ethers or mixtures thereof, heating the dispersion to reduce the vanadium, and thereafter adding phosphoric acid in an organic solvent.

In the methods described above, separation of the catalyst precursor from the reaction solution has provided difficulties. Conventionally, the solution containing the precursor must be evaporated down, usually to a catalyst precursor-containing paste which must then be dried, broken up and ground. This provides difficulties for the commercial scale-up of the process, particularly where the catalyst precursor-containing solution includes flammable organic liquids.

Where the solid phase dispersion has been maintained throughout the reduction of the vanadium and reaction with phosphoric acid, separation is more easily effected. In this instance, however, the catalyst precursor obtained is nonuniform and is difficult to process into a form acceptable for commercial use, such as pellets or tablets. The catalyst thus obtained requires high operating temperatures when used to produce maleic anhydride.

SUMMARY OF THE INVENTION

It is therefore an object of the invention to provide improved vanadium and phosphorus-containing catalysts useful for the oxidation of 4-carbon atom hydrocarbons to produce maleic anhydride.

It is a further object of the invention to provide a process of preparing vanadium and phosphorus-containing catalysts useful for the oxidation of 4-carbon atom hydrocarbons to produce maleic anhydride, which catalysts exhibit excellent yields and selectivity to maleic anhydride.

It is a further object of the invention to provide a process of preparing vanadium and phosphorus-containing catalysts useful for the oxidation of 4-carbon atom hydrocarbons to produce maleic anhydride which is simplified, highly reproducible, and economical; which avoids the hazards of corrosion and/or flammibility, and which is capable of commercial scale-up.

It is a further object of the invention to provide a process of preparing vanadium and phosphorus-containing catalysts useful for the oxidation of 4-carbon atoms hydrocarbons to produce maleic anhydride which includes improved recovery of catalyst precursors from the reaction medium.

It is a further object of the invention to provide a process of preparing vanadium and phosphorus-containing catalysts useful for the oxidation of 4-carbon atom hydrocarbons to produce maleic anhydride in which the catalyst precursors formed are highly ordered, uniform and capable of being easily processed into a commercially useful form.

These and other objects, together with the advantages thereof over known methods, which shall be apparent from the specification which follows, are accomplished by the invention as hereinafter described and claimed.

In general the process of the present invention comprises the steps of (a) introducing a substantially pentavalent vanadium-containing compound and a phosphorus-containing compound into an organic liquid medium capable of reducing the vanadium to a valence state less than +5;

(b) effecting the reduction of at least a portion of the vanadium to a valence state of +4 while in the presence of the phosphorus-containing compound;

(c) recovering the mixed vanadium phosphorus oxide-containing catalyst precursor;

(d) drying the catalyst precursor;

(e) calcining the catalyst precursor to form the active oxidation catalyst.

The catalysts prepared by the above process are particularly effective in the oxidation of 4-carbon atom hydrocarbons such as n-butane, n-butenes, 1,3 butadiene or mixtures thereof with molecular oxygen or an oxygen-containing gas in the vapor phase to produce excellent yields of maleic anhydride with very high selectivity.

Essentially all the product produced in this oxidation process is maleic anhydride, with only minor amounts of lower acids being detected.

DETAILED DESCRIPTION OF THE INVENTION

In the process of the present invention for the preparation of an oxidation catalyst containing the mixed oxides of vanadium and phosphorus, at least one vanadium compound, preferably in which a substantial portion of the vanadium is in the pentavalent state, is introduced into an organic liquid medium. Suitable vanadium compounds containing pentavalent vanadium include: vanadium pentoxide or vanadium salts, such as ammonium metavanadate and vanadium oxytrihalides. Vanadium pentoxide is preferred. The vanadium compound preferably is not readily solubilized in the organic liquid medium, but rather the reaction mixture formed is maintained in the form of a slurry.

According to the method of the present invention, at least one phosphorus-containing compound is added to the reaction mixture before substantial reduction of the vanadium to a valence state less than +5 is effected. The phosphorus compounds utilized are preferably pentavalent and suitable phosphorus compounds containing pentavalent phosphorus include: phosphoric acid, phosphorus, pentoxide, or phosphorus perhalide, such as phosphorus pentachloride. Phosphoric acid and phosphorus pentoxide are preferred.

The phosphorus-containing compound may be added to the vanadium/liquid reaction medium slurry in the form of a solution of the phosphorus-containing compound in either a component of the liquid organic reaction medium, or in a liquid capable of yielding the phosphorus-containing compound to the liquid reaction mixture. Alternatively, a vanadium compound and a phosphorus compound, such as 100% phosphoric acid, may be introduced simultaneously into the organic liquid medium. In yet another mode, the vanadium compound is introduced into a solution or dispersion of the phosphorus compound in the organic liquid medium.

It is preferred that the vanadium-containing compound which is introduced into the liquid medium have a small particle size, and methods for further reducing particle size of the vanadium compound while in the liquid medium, such as by ball milling the initial suspension of vanadium in the liquid medium, may be employed.

The organic liquid medium employed must be capable of reducing at least a portion of the vanadium to a +4 valence state, either upon addition of the vanadium compound or upon mixing and heating. In addition the liquid medium should be a solvent for phosphoric acid and be relatively unreactive towards phosphoric acid. The liquid medium should not, however, be a solvent for the mixed oxide of vanadium and phosphorus. Suitable liquid media for use in the invention are organic compounds such as alcohols, aldehydes, ketones, ethers and mixtures of the above. The organic liquid media used in the invention are preferably anhydrous. Preferred organic liquids suitable for use in this invention are alcohols, particularly isobutanol.

After the vanadium and phosphorus compounds are introduced into the liquid medium, reduction of the vanadium is effected, preferably by heating the resulting reaction mixture, with stirring if desired. The use of additional, corrosive reducing agents, such as mineral or carboxylic acids is unnecessary and undesirable, as they would tend to solubilize the vanadium-phosphorus mixed oxide and prevent the formation of the finely divided precursor precipitate which is characteristic of the invention. The precursor precipitate, when dried, has a freely flowing powdery consistency, in contrast to the caked residue which results from drying down a precursor-containing solution in which the reducing agent has solubilized the precursor.

Preferred vanadium and phosphorus oxide catalysts for the oxidation of 4-carbon atom hydrocarbons to maleic anhydride contain vanadium in an average valence state of about +3.9 to about +4.6. This average valence state is achieved when at least a portion of the pentavalent vanadium introduced into the reaction mixture is reduced to the +4 state, preferably about +4.1. As the vanadium is reduced, it is theorized that it simultaneously reacts with the phosphorus present to form the mixed vanadium phosphorus oxide.

As stated above, the liquid medium employed should not be a solvent for the vanadium-phosphorus mixed oxide. The vanadium-phosphorus oxide catalyst precursor is formed as finely divided particles which remain in dispersion form in the reaction mixture. The total $H_2O$ content of the reaction mixture, particularly at this point, should be below about 5%. The catalyst precursor is easily recovered from the reaction medium by conventional methods including filtration, centrifugation and decantation.

The catalyst precursor is then dried and calcined at a temperature of 250° C. to 600° C., preferably in the presence of an oxygen-containing gas.

The improved catalysts of the present invention exhibit improved activity, producing excellent per pass yields at high selectivity to maleic anhydride at temperatures well below those ordinarily required by vanadium phosphorus mixed oxide catalysts for the conversion of 4-carbon atom hydrocarbons to maleic anhydride. Additionally, we found the improved catalysts of the present invention to be exceptionally reproducible, and to be unexpectedly highly ordered and extremely uniform in physical structure, resulting in facile processibility to achieve commercial fixed or fluid-bed forms, such as pellets, tablets or coated particles.

The surprising uniformity and order of the catalysts are evidenced by the crystalline structure and surface textural characteristics exhibited in FIGS. 1–16, which are scanning electron micrographs of (a) the vanadium compound reagent preferably used in the preparation of the vanadium phosphorus mixed oxide catalysts; (b) vanadium phosphorus mixed oxide precursors and catalysts prepared by known methods; and (c) vanadium phosphorus mixed oxide precursors and catalysts prepared by the process of the present invention.

The micrographs of FIGS. 1–16 were prepared according to standard scanning electron microscopic techniques. In each instance, the sample particles were sprinkled on a support stud which had been coated with silver polish. The samples were then gold coated to render them conductive in order to prevent charging. The samples were examined by an AMR scanning electron microscope.

Figure 1:
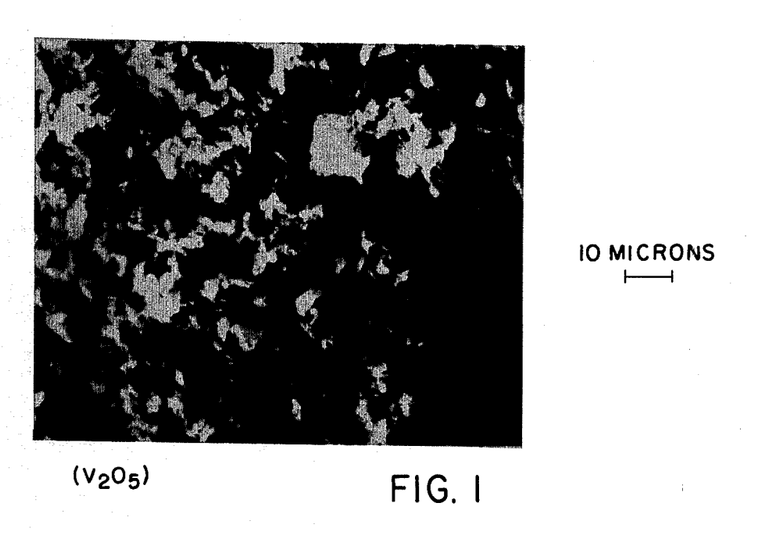
FIG. 1 is a scanning electron micrograph of vanadium pentoxide particles at 1,000× magnification.
Figure 2:
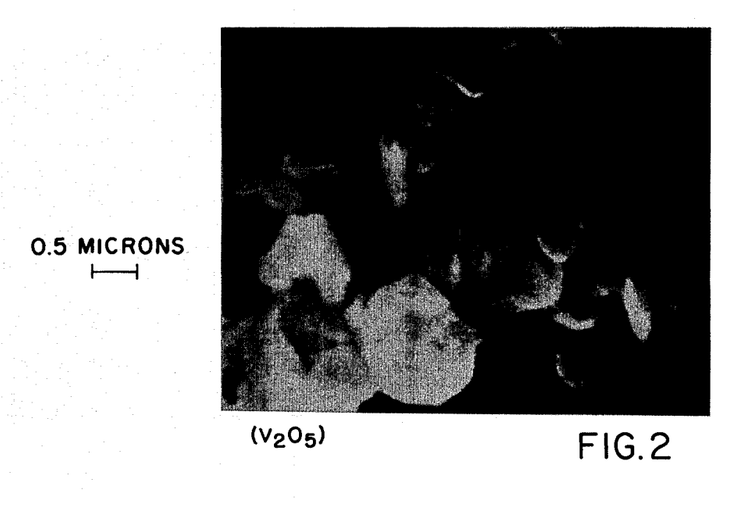
FIG. 2 is a scanning electron micrograph of vanadium pentoxide particles at a 20,000× magnification.

FIGS. 1 and 2 are scanning electron micrographs of vanadium pentoxide at 1,000× and 2,000× magnification, respectively. The vanadium pentoxide particles appear to be predominantly platelet in form.

Figure 3:
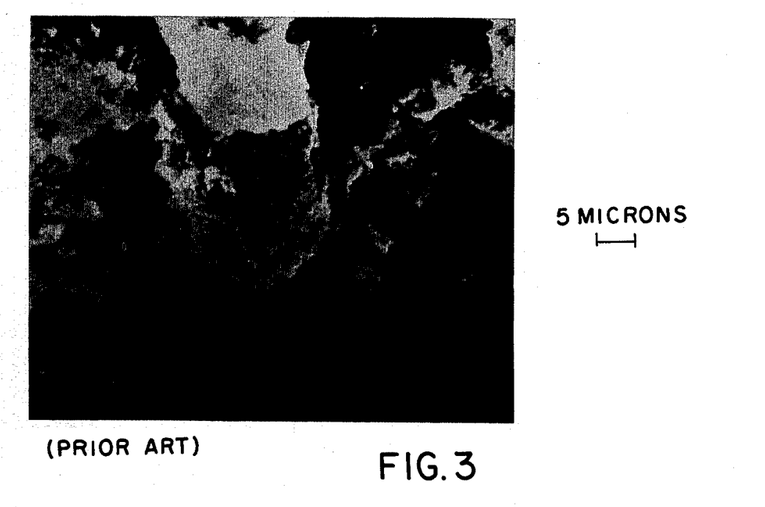
FIG. 3 is a scanning electron micrograph of vanadium phosphorus mixed oxide catalyst particles, prepared by HCl reduction of $V_2O_5$ in isobutanol and which have been calcined and used in the preparation of maleic anhydride from n-butane, at a 2,000× magnification.
Figure 4:
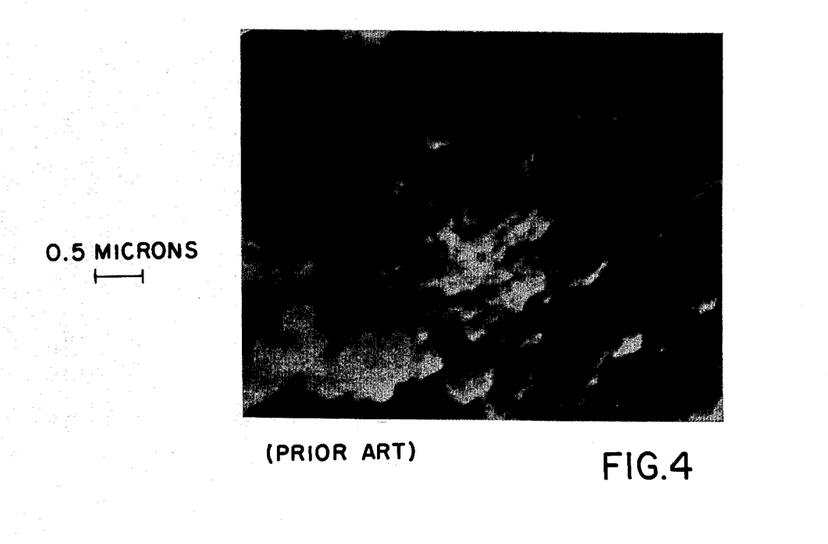
FIG. 4 is a scanning electron micrograph of vanadium phosphorus mixed catalyst particles, prepared by HCl reduction of $V_2O_5$ in isobutanol and which have been calcined and used in the preparation of maleic anhydride from n-butane, at 20,000× magnification.
Figure 5:
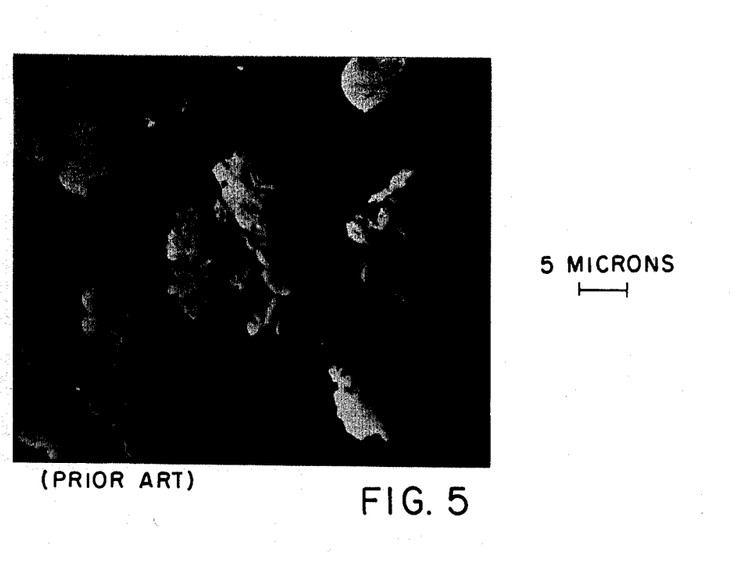
FIG. 5 is a scanning electron micrograph of vanadium phosphorus mixed oxide catalyst particles, prepared by reduction of vanadium pentoxide in an isobutanol slurry prior to contacting the same with phosphoric acid, and which were calcined for 2 hours at 400° C., at a 2,000× magnification.
Figure 6:
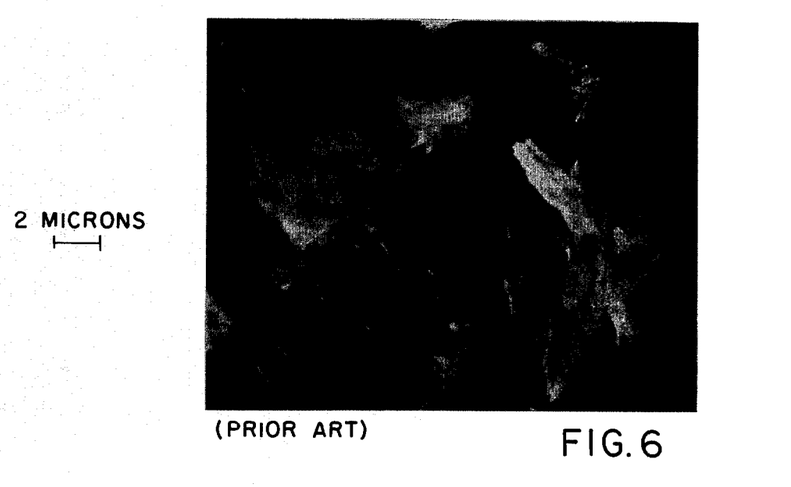
FIG. 6 is a scanning electron micrograph of vanadium phosphorus mixed oxide precursor particles, prepared by reduction of vanadium pentoxide in an isobutanol slurry prior to contacting the same with phosphoric acid, at a 5,000× magnification.
Figure 7:
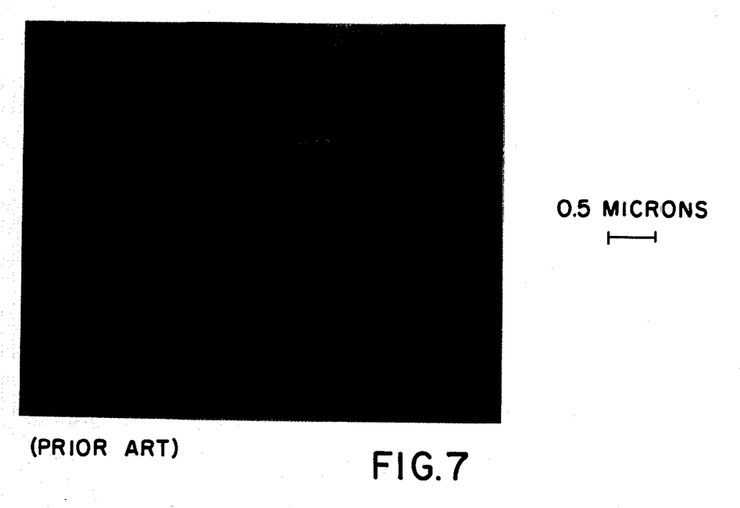
FIG. 7 is a scanning electron micrograph of vanadium phosphorus mixed oxide precursor particles, prepared by reduction of vanadium pentoxide in an isobutanol slurry prior to contacting the same with phosphoric acid, at a 20,000× magnification.
Figure 8:
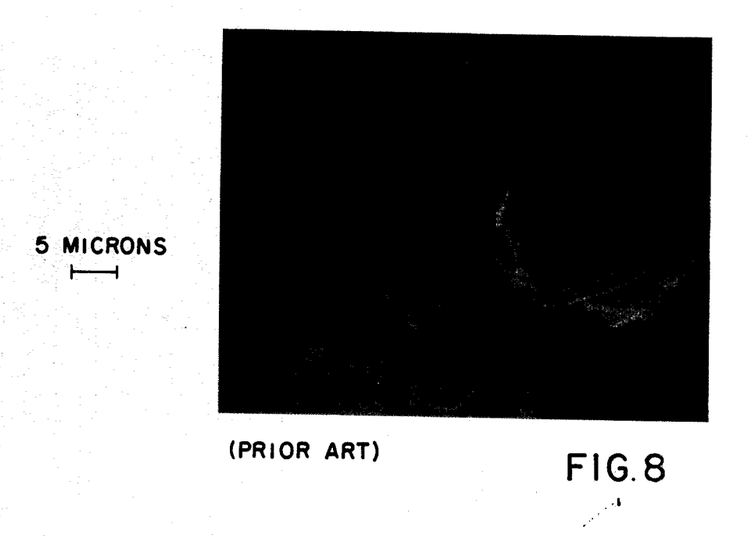
FIG. 8 is a scanning electron micrograph of vanadium phosphorus mixed oxide catalyst particles, prepared by reduction of vanadium pentoxide in an isobutanol slurry prior to contacting the same with phosphoric acid and which have been calcined for 2 hours at 400° C., at a 20,000× magnification.

FIGS. 3 and 4 are scanning electron micrographs of vanadium phosphorus mixed oxide catalyst particles prepared by HCl reduction of vanadium pentoxide, calcined and used, at 2,000× and 20,000× magnification respectively. Both the precursor (not shown) and the catalyst particles prepared in this manner are generally amorphous in textural characteristics. In order to recover the precursor from solution, the solvent is evaporated first down to a paste, and then to a solid cake, which must be broken up and ground to the desired particle size, resulting in the amorphous physical form which persists through calcination and use.

FIGS. 5–8 are scanning electron micrographs of vanadium phosphorus mixed oxide precursor and catalyst particles, prepared by reduction of vanadium pentoxide in an isobutanol slurry prior to contacting the same with phosphoric acid, at from 2,000× to 20,000× magnification. These precursors and catalysts both appear to consist predominantly of small groups of associated platelets, each individual platelet being similar in structure and textural characteristics to the structure of the vanadium pentoxide reactant used in their preparation. The general macrostructure of the precursors and catalysts is that of a flattened disk, with the associated platelets which make up the disk being arranged so as to resemble the petals of a flower, the platelets generally contacting each other at their edges.

Figure 9:
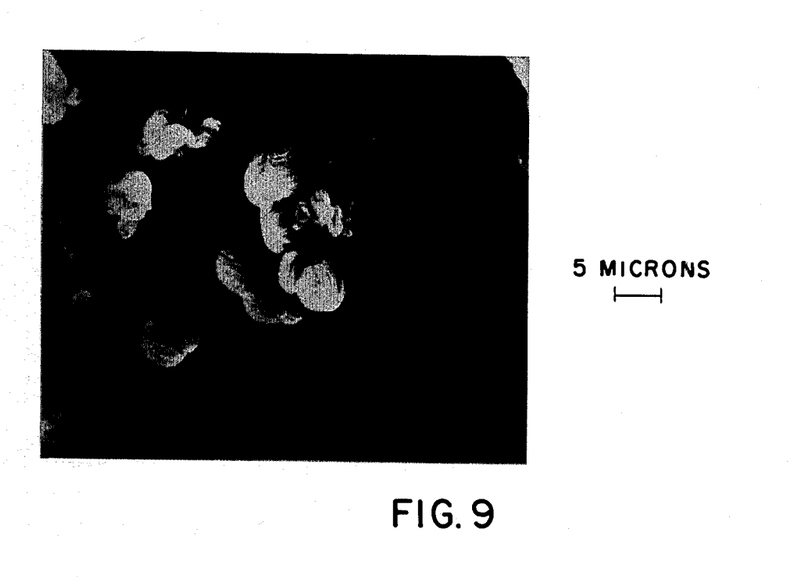
FIG. 9 is a scanning electron micrograph of vanadium phosphorus mixed oxide precursor particles prepared according to the process of the present invention, at a 2,000× magnification.
Figure 10:
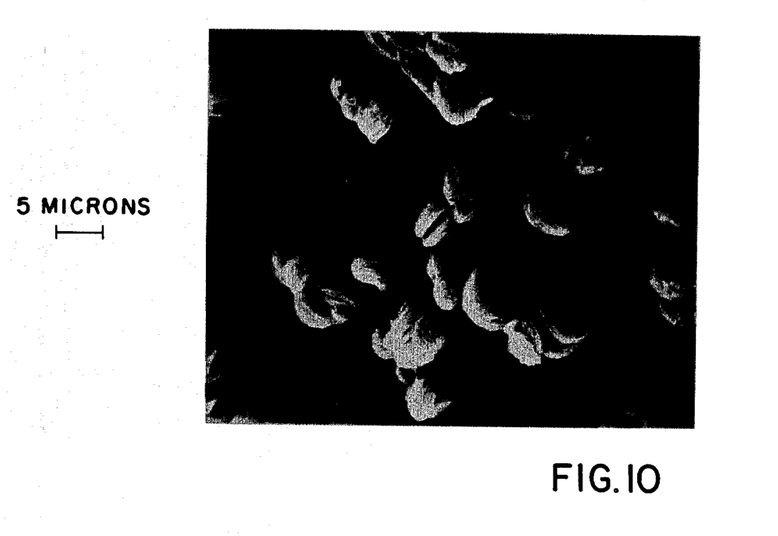
FIG. 10 is a scanning electron micrograph of vanadium phosphorus mixed oxide catalyst particles prepared according to the process of the present invention and calcined for one and one-half hours at 400° C., at a 2,000× magnification.
Figure 11:
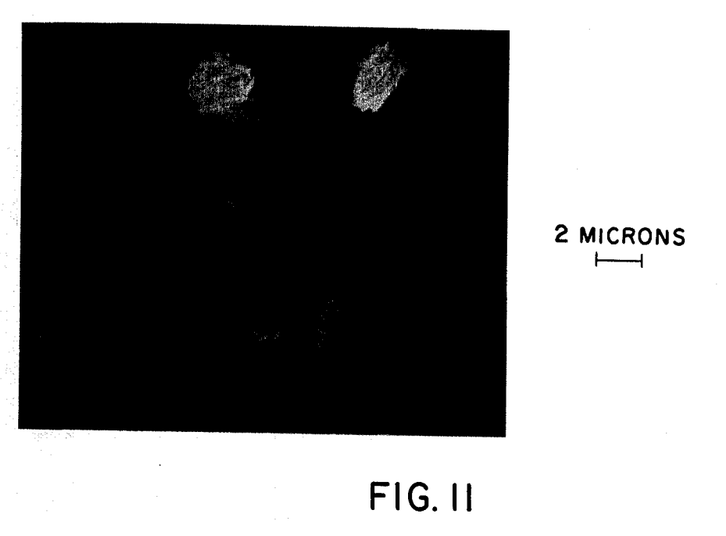
FIG. 11 is a scanning electron micrograph of vanadium phosphorus mixed oxide precursor particles prepared according to the process of the present invention, at a 5,000× magnification.
Figure 12:
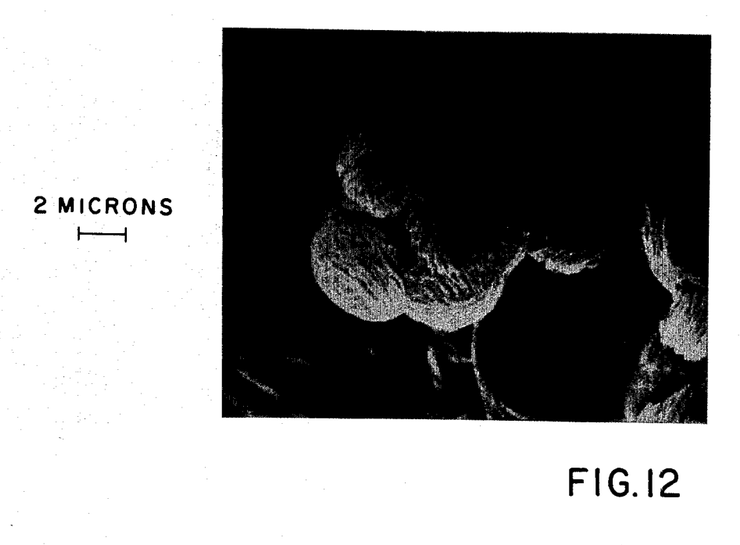
FIG. 12 is a scanning electron micrograph of vanadium phosphorus mixed oxide catalyst particles prepared according to the process of the present invention and calcined for one-half hour at 400° C., at a 5,000× magnification.
Figure 13:
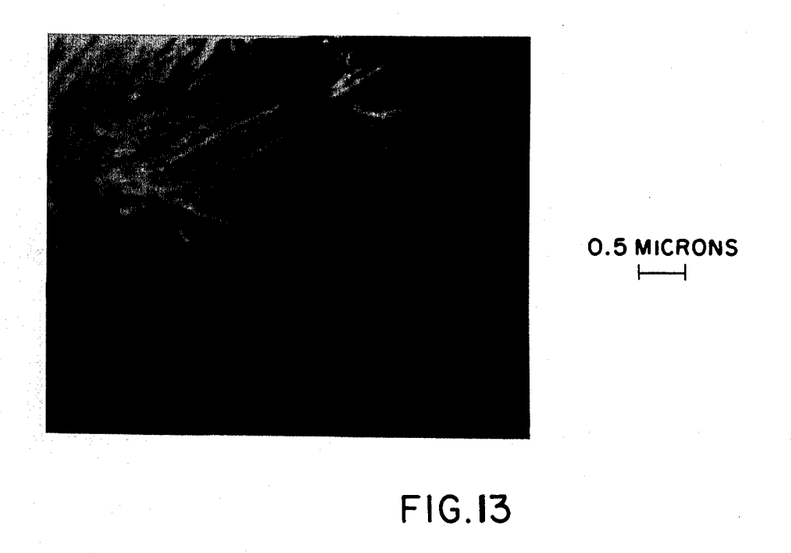
FIG. 13 is a scanning electron micrograph of vanadium phosphorus mixed oxide precursor particles prepared according to the process of the present invention, at a 20,000× magnification.
Figure 14:
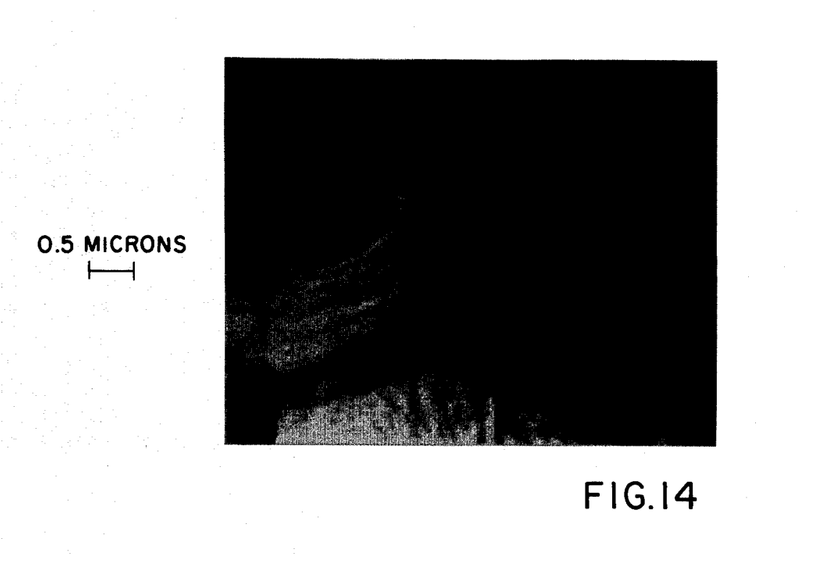
FIG. 14 is a scanning electron micrograph of vanadium phosphorus mixed oxide precursor particles prepared according to the process of the present invention, at a 20,000× magnification.
Figure 15:
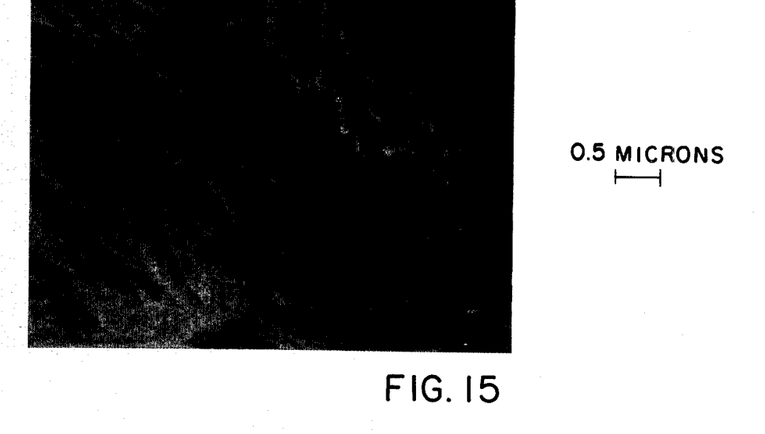
FIG. 15 is a scanning electron micrograph of vanadium phosphorus mixed oxide catalyst particles prepared according to the process of the present invention, and calcined for one-half hour at 400° C., at a 20,000× magnification.
Figure 16:
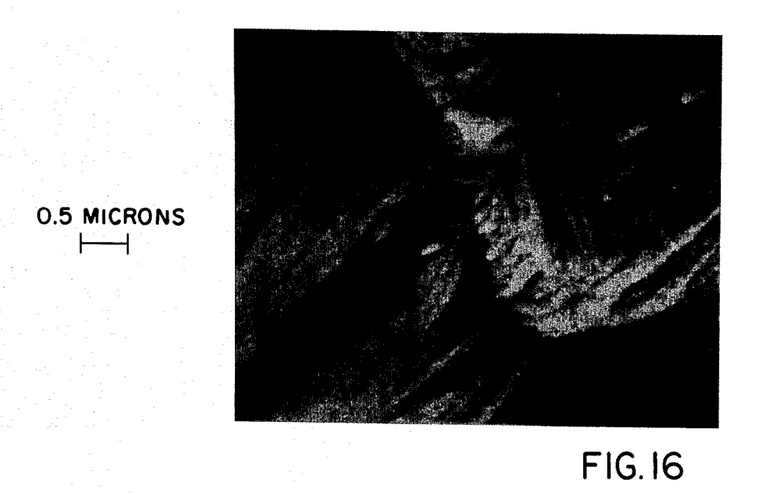
FIG. 16 is a scanning electron micrograph of vanadium phosphorus mixed oxide catalyst particles prepared according to the process of the present invention, and calcined for one and one-half hours at 400° C., at a 20,000× magnification.

FIGS. 9–16 are scanning electron micrographs of precursors and catalysts prepared according to the process of the present invention. The precursors and catalysts of the present invention exhibit an unexpectedly highly ordered and uniform spheroid type crystalline macrostructure. This structure appears to comprise a stack of sheets of catalytic material; the sheets being integrally associated with each other, yet in partially spaced apart relation to one another at the edges, not unlike a stack of dinner plates. The structure of the precursors and catalysts according to the invention, as can be seen in FIGS. 9 and 10 respectively, resemble in their textural characteristics, windings of yarn, however, it should be noted that the individual "strings" are actually edges of the sheets of catalytic material. This is more apparent at higher magnifications, such as in FIGS. 11–16. The stacked sheet structure predominates among the precursors and catalysts of the invention, although the sheets may become somewhat convoluted as shown in FIG. 14, in which it can be seen that even in this confirmation the sheets maintain their integrally stacked, partially spaced apart relation to each other.

Comparing the precursor and catalyst particles of the invention with those known in the prior art, it appears that the process of the present invention provides a far greater density of active catalytic material, and thus a greater number of active catalytic sites per volume of catalytst which is presented to the exterior, that is being made available to the hydrocarbon and oxygen reactants in order to aid in the preparation of maleic anhydride. The precursor and catalyst particles of the present invention are predominantly more ordered and more uniform than those produced by prior art techniques.

The catalyst precursors prepared by the method of the present invention exhibit extremely small particle size. The particle size of the catalyst precursor prepared according to the process of the present invention, a specific embodiment of which is set forth below in Examples 1-7, was measured by the change in resistance of an electrolyte induced by the reduction of a standard volume of the electrolyte due to the presence of the catalyst precursor particles, using an Electrozone/Celloscope available from Particle Data, Inc., Elmhurst, Ill. At least 50% of the catalyst precursor particles exhibited an average diameter of less than 11 microns when measured by this technique. The percentage of catalyst precursor particles having an average diameter less than 6, 10, 16.2, 19.5 and 25.1 microns are set forth in Table 1 below.

The very small particle size of the catalysts of the present invention, permits the incorporation of the catalytic material into commercially suitable form. If the catalyst particles are desired which are smaller than those obtained by the process of the present invention, the particles can be comminuted, such as by ball milling, before calcining and forming into commercial catalysts. Because the precursor and catalyst particles of the present invention are so finely divided and uniform, extensive comminution is not required, so that the highly ordered and uniform structure obtained by the use of the process of the invention is not lost when the catalytic material is converted to a commercial form.

Catalysts prepared according to the process of the present invention possess a characteristically high intrinsic surface area as measured by the technique described in 60 JACS 309 (1938). It is reported in the literature that nonpromoted mixed oxides of vanadium and phosphorus have been prepared which have intrinsic surface areas of up to 28 $m^2/g$. The catalysts prepared by the method of the invention, however, exhibit an intrinsic surface area of from about 25 $m^2/g$ to about 60 $m^2/g$, even when consisting essentially of the mixed oxides of vanadium and phosphorus, that is, in the absence of promotional elements which would tend to cause an increase in intrinsic surface area of the mixed oxide due to their presence.

It is within the scope of this invention, however, to include promoter element-containing compounds in the reaction mixture at a suitable point in order that the catalyst precursor contain the promoter element, if desired.

Catalysts prepared by the method of the invention generally exhibit a phosphorus to vanadium ratio of about 1:1 to about 1.2:1. Preferred is a P/V ratio of about 1.1:1 to about 1.2:1. The catalyst is activated by calcining it in air or an oxygen-containing gas at a temperature of 250° C. to 600° C. for a period of up to 5 hours or more. A preferred activation of the catalyst is accomplished by passing a mixture of steam and air or air alone over the catalyst at a temperature of about 300° C. to 500° C. for a period of about ½ hour to 5 hours.

The hydrocarbon reacted to form maleic anhydride may be n-butane, n-butenes, 1,3-butadiene, or a mixture thereof. Preferred is the use of n-butane or a mixture of hydrocarbons that are produced in refinery streams. The molecular oxygen is most conveniently added as air, but synthetic streams containing molecular oxygen are also suitable. In addition to the hydrocarbon and molecular oxygen, other gases may be added to the reactant feed. For example, steam or nitrogen could be added to the reactants.

The ratio of the reactants may vary widely and are not critical. The ratio of molecular oxygen to the hydrocarbon may range from about 2 to about 30 moles of oxygen-per mole of hydrocarbon. Preferred oxygen/hydrocarbon ratios are about 4 to about 20 moles of oxygen per mole of hydrocarbon.

The reaction temperature may vary widely and is dependent upon the particular hydrocarbon and the form of the catalyst employed. Normally, temperatures of about 250° C. to about 600° C. are employed with temperatures of 350° C. to 450° C. being preferred.

The catalyst may be used alone or a support could be employed. Suitable supports include silica, alumina, Alundum, silicon carbide, titania, boron phosphate, zirconia, and the like. The catalysts may be used in a fixed-bed reactor using tablets, pellets or the like, or in a fluid-bed reactor using catalysts preferably having a particle size of less than about 300 microns. The contact time may be as low as a fraction of a second or as high as 50 seconds. The reaction may be conducted at atmospheric, superatmospheric or subatmospheric pressure.

EXAMPLES 1-7

According to the process of the present invention, 909.5 g $V_2O_5$ (technical grade) was added to 13 liters of technical grade isobutanol. Stirring was begun and a solution of 1176 g $H_3PO_4$ (100%) in 2 liters isobutanol was added to form a dark yellow slurry which deepened in color on subsequent heating to reflux temperature.

After refluxing for about 16 hours, stirring was continued and the slurry was allowed to cool. A light blue precipitate was filtered from the slurry, and dried at ambient temperature under vacuum. The precipitate was washed with about 1 liter isobutanol, partially dried at ambient temperature under a vacuum, and then dried for 2½ hours at about 145° C.

A portion of the precipitate, 63.3 g, was calcined for one hour at about 400° C. The calcined catalyst powder was formed into 3/16 inch (0.48 cm) tablets on a Stokes press using 1.65 g stearic acid. The resulting catalysts are represented by the formula $V_{1.0}P_{1.2}O_x$ where x is the number of oxygens required to satisfy the valence requirements of the other elements.

COMPARATIVE EXAMPLES 8-11

Catalysts represented by the formula $V_{1.0}P_{1.2}O_x$ were prepared in the following manner. 1008 g $V_2O_5$ (technical grade) was added to 5.5 liters isobutanol (technical grade). The resulting slurry was stirred while anhydrous hydrogen chloride gas (technical grade) was bubbled through the reaction medium. The temperature of the reaction medium was maintained at 20°±5° C. by use of a cooling bath.

After approximately 4 hours, the temperature of the homogenous solution began to drop, indicating completion of the exothermic vanadium reduction reaction. A solution of 1303 g orthophosphoric acid in 2 liters isobutanol was added to the reaction medium. The reaction medium was then refluxed for 1.5 hours, at which time the previously brownish solution attained a dark blue-green color. The solution was dried via evaporation in a pot furnace controlled at a temperature of about 150° C. for about 16 hours. The resulting solid was crushed and ground to pass through 50 mesh (0.30 mm) screen. The resulting powder was pressed into 3/16 inch (0.48 cm) tablets and calcined at about 400° C. for about 16 hours.

COMPARATIVE EXAMPLES 12–15

Catalysts represented by the formula $V_{1.0}P_{1.2}O_x$ were prepared in the following manner. 80 g $V_2O_5$ technical grade was introduced into 700 ml isobutanol with mechanical stirring and was refluxed for about 16 hours, resulting in an olive-green slurry. 100 g of 100% orthophosphoric acid was dissolved in isobutanol and added to the slurry. The reaction mixture was refluxed for about 8 hours after which it was allowed to cool and stand. The suspension was then filtered to yield a greenish-blue solid which was dried for 2 hours at about 150° C. The catalyst precursor was then tabletted with 1% graphite in a Buehler Press to 1⅛ inch (about 2.84 cm) diameter. The tablets were then calcined in air from 200° C. to 400° C. at a rate of 5° C. per minute, being held at 400° C. for one hour. These were ground and screened to 30 mesh (0.6 mm) before use.

COMPARATIVE EXAMPLES 16–18

The procedure of Examples 12–15 was repeated, and the resulting catalyst powder was pressed into 3/16 inch (0.48 cm) tablets on a Stokes press with 1.65 g stearic acid after calcination at 400° C. for one hour.

The catalysts described in Examples 1–7 and Comparative Examples 8–18 were used to produce maleic anhydride from butane using a 20 cc fixed-bed reactor consisting of a length of stainless steel tubing having an outer diameter of about 1.3 cm and having a full length 0.31 cm axial thermowell. The reactor was heated with a split stainless steel block furnace. Flasks for receiving the product maleic anhydride were mounted in ice water, and tail gases were routed to a Carle Analytical Gas Chromatograph III for analysis. Reaction conditions and results of the test runs are described in Table II. The results are stated in terms as follows:

$$\text{Single Pass Yield} = \frac{\text{Moles of Maleic Anhydride Formed}}{\text{Moles of Butane Fed}} \times 100$$

$$\text{Total Conversion} = \frac{\text{Moles of Butane Reacted}}{\text{Moles of Butane Fed}} \times 100$$

$$\text{Selectivity} = \frac{\text{Single Pass Yield} \times 100}{\text{Total Conversion}}$$

When the for preparing catalysts containing mixed oxides of vanadium and phosphorus is employed according to the present invention, the hazards presented by using highly corrosive materials such as HCl gas are avoided. In addition, the vanadium and phosphorus-containing catalyst precursor can be separated from the reaction medium simply by filtration or similar methods, avoiding the hazards of evaporating off large quantities of flammable liquid. The spent liquid reaction medium utilized in the process of the present invention, after the catalyst precursor has been removed, may easily be recycled for use in the reaction again. These features of the process of the invention permit efficient commercial scaleup of the process.

As can be seen from the results listed in Table II, the improved catalysts prepared according to the method of the invention effect excellent yields and selectivities of 4 carbon atom hydrocarbons, such as butane, to maleic anhydride at lower reaction temperatures than would be feasible for catalysts prepared by known techniques. The method of the present invention produces catalysts having highly reproducible characteristics, in terms of not only their highly ordered and uniform physical form, but also in their catalytic activity. Additionally, post preparation formation of the catalytic material into commercially usable forms is aided when the catalytic material utilized is prepared according to the method of the invention.

Thus it should be apparent to those skilled in the art that the subject invention accomplishes the objects set forth above. It is to be understood that the subject invention is not to be limited by the examples set forth herein. These have been provided merely to demonstrate operability, and the selection of vanadium and phosphorus-containing compounds, liquid media, promoter element-containing compounds if any, hydrocarbon feedstocks and reaction conditions can be determined from the total specification disclosure provided, without departing from the spirit of the invention herein disclosed and described, the scope of the invention including modifications and variations that fall within the scope of the attached claims.

TABLE I

| Sample | Percentage of Particles Having an Average Diameter of less Than: | | | | |
|---|---|---|---|---|---|
| | 6μ | 10μ | 16.2μ | 19.5μ | 25.1μ |
| A | 29.7 | 48.6 | 68.4 | 78 | 88.4 |
| B* | 28.1 | 51.3 | 76.6 | 87 | 93.3 |
| C | 28.1 | 48.7 | 69.9 | 80 | 89.2 |

*Calcined for 1 hour at 400° C.

TABLE II

Preparation of Maleic Anhydride From N-Butane Using $V_{1.0}P_{1.2}O_x$ Catalysts

| Example No. | Temperature °C. | Air/HC Ratio | Contact Time Seconds | Maleic Anhydride Molar % | |
|---|---|---|---|---|---|
| | | | | Yield | Selectivity |
| 1 | 380 | 70 | 2 | 54.2 | 60.6 |
| 2 | 380 | 70 | 2 | 53.2 | 61.2 |
| 3 | 371 | 70 | 2 | 51.4 | 64.5 |
| 4 | 390 | 73 | 2 | 54.3 | 58.7 |
| 5* | 400 | 70 | 2 | 59.2 | 64.9 |
| 6* | 390 | 70 | 2 | 55.7 | 65.3 |
| 7 | 395 | 70 | 2 | 59.5 | 68.1 |
| C8 | 425 | 62 | 1 | 38.4 | 55.2 |
| C9 | 430 | 70 | 2 | 51.6 | 59.7 |
| C10 | 435 | 70 | 2 | 51.1 | 56.7 |
| C11 | 440 | 70 | 2 | 49.9 | 54.8 |
| C12 | 446 | 67 | 1 | 52.2 | 55.1 |
| C13 | 431 | 67 | 2 | 56.1 | 59.1 |
| C14 | 430 | 67 | 2 | 54.3 | 61.4 |
| C15 | 398 | 67 | 3 | 45.4 | 66.6 |
| C16 | 398 | 70 | 2 | 35.0 | 69.5 |
| C17 | 429 | 70 | 2 | 56.7 | 61.7 |
| C18 | 432 | 70 | 2 | 54.7 | 62.4 |

Tail Gas Analysis

We claim:

1. A process for the production of maleic anhydride by the oxidation of n-butane, n-butene, 1,3 butadiene or a mixture thereof with molecular oxygen or an oxygen-containing gas in the vapor phase at a reaction temperature of 250° C.–600° C. in the presence of a catalyst containing the mixed oxides of vanadium and phosphorus, wherein said catalyst is prepared by
  (a) introducing a substantially pentavalent vanadium-containing compound and a pentavalent phosphorus-containing compound into an organic liquid medium capable of reducing the vanadium to a valence state less than +5;

(b) effecting the reduction of at least a portion of the vanadium to a valence state of +4 while in the presence of the phosphorus-containing compound and in the absence of a corrosive reducing agent by heating the vanadium-containing reducing medium of step (a);

(c) recovering the mixed vanadium phosphorus oxide-containing catalyst precursor;

(d) drying the catalyst precursor;

(e) calcining the catalyst precursor to form the active oxidation catalyst.

2. A process as recited in claim 1 wherein said organic liquid medium is essentially anhydrous.

3. A process as recited in claim 1 wherein reduction of said vanadium is effected by heating the vanadium-containing reaction medium of step (a) under reflux conditions.

4. A process as recited in claim 1 wherein said vanadium-containing compound is added to a solution or dispersion of said phosphorus-containing compound in the organic liquid medium.

5. A process as recited in claim 1 wherein said phosphorus-containing compound is added to a slurry or suspension of said vanadium-containing compound in the organic liquid medium.

6. A process as recited in claim 1 wherein said pentavalent phosphorus-containing compound is added to the reaction medium in the form of a solution of said phosphorus-containing compound in said organic liquid.

7. A process as recited in claim 1 wherein said organic liquid is selected from the group consisting of alcohols, ketones, aldehydes, ethers and mixtures thereof.

8. A process as recited in claim 1 wherein said organic liquid is an alcohol.

9. A process as recited in claim 8 wherein said organic liquid is isobutanol.

10. A process as recited in claim 1 wherein said vanadium-containing compound is vanadium pentoxide.

11. A process as recited in claim 1 wherein said phosphorus-containing compound is orthophosphoric acid.

12. A process as recited in claim 1 wherein said oxidation catalyst is represented by the empirical formula:

$$V_1P_aO_x$$

wherein
a = 1.0 to 1.2 and x is the number of oxygens required to satisfy the valence requirements of the other elements.

13. A process for the production of maleic anhydride by the oxidation of n-butane, n-butene, 1,3-butadiene or a mixture thereof with molecular oxygen or an oxygen-containing gas in the vapor phase at a reaction temperature of 250° C.–600° C. in the presence of a catalyst comprising the mixed oxides of vanadium and phosphorus, said catalyst characterized by an average valence state of vanadium from about +3.9 to about +4.6, a phosphorus to vanadium ratio of about 1:1 to about 1.2:1, wherein the macrostructure of the catalyst predominantly comprises generally spheroid particles consisting of stacks of integrally associated sheets of catalytic material.

14. A process as recited in claim 13, wherein at least 75 percent of the particles have an average diameter of less than about 25 microns.

15. A process as recited in claim 13, wherein at least 75 percent of the particles have an average diameter of less than about 20 microns.

16. A process as recited in claim 13, wherein said catalyst has an intrinsic surface area of about 25 m²/g to about 60 m²/g.

* * * * *